(12) United States Patent
Roller et al.

(10) Patent No.: US 8,197,480 B2
(45) Date of Patent: *Jun. 12, 2012

(54) BIOABSORBABLE COATINGS OF SURGICAL DEVICES

(75) Inventors: Mark B. Roller, New Brunswick, NJ (US); Joseph Contiliano, Stewartsville, NJ (US); Kevin L. Cooper, Flemington, NJ (US); Jo Hays, Logan, UT (US); Jenny J. Yuan, Neshanic Station, NJ (US)

(73) Assignee: DePuy Mitek, Inc., Raynham, MA (US)

( * ) Notice: Subject to any disclaimer, the term of this patent is extended or adjusted under 35 U.S.C. 154(b) by 73 days.

This patent is subject to a terminal disclaimer.

(21) Appl. No.: 12/748,866

(22) Filed: Mar. 29, 2010

(65) Prior Publication Data

US 2010/0185199 A1    Jul. 22, 2010

Related U.S. Application Data

(63) Continuation of application No. 10/027,891, filed on Dec. 20, 2001, now Pat. No. 7,713,272.

(51) Int. Cl.
*A61B 17/56* (2006.01)

(52) U.S. Cl. .............................. 606/77; 606/76; 606/60

(58) Field of Classification Search .................... 606/77, 606/76, 70, 79, 219, 220, 155, 60; 623/23.75, 623/23.51, 1.42; 523/113
See application file for complete search history.

(56) References Cited

U.S. PATENT DOCUMENTS

| | | | |
|---|---|---|---|
| 3,527,650 A | 9/1970 | Block | |
| 4,547,542 A | 10/1985 | Lundberg et al. | |
| 4,705,820 A | 11/1987 | Wang et al. | |
| 4,788,979 A | 12/1988 | Jarrett et al. | |
| 4,994,074 A | 2/1991 | Bezwada et al. | |
| 5,100,433 A | 3/1992 | Bezwada et al. | |
| 5,108,399 A | 4/1992 | Eitenmuller et al. | |
| 5,275,601 A | 1/1994 | Gogolewski et al. | |
| 5,352,515 A * | 10/1994 | Jarrett et al. | 428/357 |
| 5,364,400 A | 11/1994 | Rego, Jr. et al. | |
| 5,383,903 A | 1/1995 | Totakura | |
| 5,458,653 A | 10/1995 | Davidson | |
| 5,505,736 A * | 4/1996 | Reimels et al. | 606/318 |
| 5,543,218 A | 8/1996 | Bennett et al. | |
| 5,571,139 A | 11/1996 | Jenkins, Jr. | |
| 5,591,997 A | 1/1997 | Guidash et al. | |
| 5,621,050 A | 4/1997 | Jarrett et al. | |
| 5,854,383 A | 12/1998 | Erneta et al. | |
| 5,951,560 A | 9/1999 | Simon et al. | |
| 5,951,997 A | 9/1999 | Bezwada et al. | |
| 5,984,927 A | 11/1999 | Wenstrom, Jr. et al. | |
| 6,022,350 A | 2/2000 | Ganem | |

(Continued)

FOREIGN PATENT DOCUMENTS

EP     0360139 A2     3/1990

(Continued)

OTHER PUBLICATIONS

Euopean Search Report dated Nov. 25, 2003, for corresponding EP 02258785.1.

*Primary Examiner* — Pedro Philogene

(57) ABSTRACT

Bioabsorbable coatings for bioabsorbable implantable medical devices having dragging or engagement surfaces. The coatings on a surface of the devices reduce device drag.

18 Claims, 4 Drawing Sheets

U.S. PATENT DOCUMENTS

| | | |
|---|---|---|
| 6,045,581 A | 4/2000 | Burkinshaw |
| 6,093,201 A | 7/2000 | Cooper et al. |
| 6,197,320 B1 | 3/2001 | Shalaby |
| 6,206,883 B1 * | 3/2001 | Tunc .............................. 606/77 |
| 6,221,075 B1 * | 4/2001 | Tormala et al. ................. 606/77 |
| 6,287,324 B1 | 9/2001 | Yarnitsky et al. |
| 6,458,867 B1 * | 10/2002 | Wang et al. .................... 523/105 |
| 6,530,933 B1 | 3/2003 | Yeung et al. |
| 6,554,862 B2 * | 4/2003 | Hays et al. ................. 623/13.14 |
| 6,626,939 B1 | 9/2003 | Burnside et al. |
| 6,685,706 B2 | 2/2004 | Padget et al. |
| 6,846,313 B1 | 1/2005 | Rogers et al. |
| 7,713,272 B2 * | 5/2010 | Roller et al. .................... 606/77 |
| 2004/0082998 A1 | 4/2004 | Shinomiya et al. |

FOREIGN PATENT DOCUMENTS

| | | |
|---|---|---|
| EP | 0441537 A1 | 8/1991 |
| WO | 9315682 A1 | 8/1993 |

\* cited by examiner

BIOABSORBABLE COATINGS OF SURGICAL DEVICES

CROSS-REFERENCE TO RELATED APPLICATIONS

This application is a continuation of U.S. patent application Ser. No. 10/027,891 filed on Dec. 20, 2001 and entitled "Bioabsorbable Coatings of Surgical Devices", which is hereby incorporated by reference in its entirety.

FIELD OF THE INVENTION

The present invention relates to bioabsorbable coatings for implantable medical devices, more specifically, to bioabsorbable implantable medical devices with improved lubricity.

BACKGROUND OF THE INVENTION

In medical procedures, the movement of a surface of an implantable device with respect to tissue is important in reducing damage to both the surface and to the tissue. Damage to tissue as a result of "tissue drag" friction is know to cause inflammation and pain, and may lead to a longer recovery time. High friction between a surface material of an implant and blood may result in clotting and subsequent occlusion of a blood vessel. Friction may also damage the implant material, thus rendering it ineffective or shortening its useful life.

The problem of "tissue drag" has been of concern to the medical profession for some time. For example, it is know to improve the lubricity of a braided polyethylene terephthalate suture by applying a coating to the outer surface of the suture consisting of polymers of polyethylene or polytetrafluoroethylene (PTFE) having a lower coefficient of friction than the surface of the suture. It is also known that sutures coated with dimethylsiloxane-alkylene oxide copolymers have improved handling characteristics. These polymers, however, are not bioabsorbable, and therefore leave a residue in the tissue.

The use of certain bioabsorbable polymers as coatings to improve the tie-down performance of sutures and to also reduce tissue drag is similarly known in this art. These coatings may include copolymers and blends containing monomers of lactide, glycolide, epsilon-caprolactone, trimethylene carbonate, p-dioxanone, ethylene oxide, and propylene oxide.

The reduction of tissue drag using bioabsorbable polymers as coatings on implantable medical devices other than sutures has also known. The coated devices include, for example, screws and suture anchors, having surfaces that drag along and contact both soft and hard tissue during implantation.

Many implantable medical devices, such as hip or knee prostheses, are structured such that, during their life, or during the medical procedure for implantation, there is movement of a surface of the device against another surface of the device. This relative movement, or articulation, of one surface against another, is known as "device drag". In device drag, friction may damage the material of the surface, thus rendering it ineffective or shortening its useful life.

The issues of device drag in non-bioabsorbable implantable medical devices have been addressed in a variety of ways. For example, it is known to apply a thin layer of a low coefficient of friction coating (ceramic or diamond-like carbon) on one or more contact surfaces. Such a coating reduces friction between the surfaces of a bone fixing device formed from conventional implantable materials such as titanium alloys and solids ceramics.

Also, with regard to implantable orthopedic prostheses having a metallic first component having a first bearing surface, and a second metallic component having a second bearing surface, where the second bearing surface is disposed in opposition to the first bearing surface in a sliding bearing relationship, it is known to provide on at least one of the first and second bearing surfaces a plurality of substantially evenly distributed plateaus interspersed with valleys. The valleys have a depth of about 0.0002 inch to about 0.002 inch below the plateaus to facilitate lubrication of the articulating surfaces by natural body fluids.

Although the issue of device drag has been addressed in non-bioabsorbable implantable medical devices, there is a desire in many applications to move away from non-absorbable implants. A major disadvantage of non-bioabsorbable implantable medical devices is that they remain permanently in the body. It is known that these implants can cause a variety of problems after healing, for example, chronic irritation and inflammation of surrounding body tissue, abrading of tissue during normal motion of the joint, and problems in X-ray imaging in follow-up examinations since the implant may block out the view of the tissue. When complications do arise from non-bioabsorbable implantable medical devices additional surgical procedures may be required to remove problematic devices once the tissue has healed, placing the patient at additional risk.

Bioabsorbable implantable medical devices are naturally degradable by the body, through known mechanisms including bioresorption and biodegradation. Accordingly, contact with surrounding tissue after implantation does not necessitate surgical intervention because the device will be completely absorbed by the body once the tissue has healed. Reducing device drag is particularly advantageous in polymeric bioabsorbable devices where the device is inserted in hard body tissues such as bone using a driver that engages the device. The driver/device connection or engagement location is susceptible to failure if the load resulting from tissue drag exceeds the strength of such connection or engagement location. By reducing tissue drag, the load necessary to insert the device is typically decreased, reducing the risk of failure at the driver/device connection, or failure to other parts of the device as well.

The problems of tissue drag and device drag in implantable medical devices have been of concern to the medical profession for some time. In implantable devices that drag along tissue, both non-bioabsorbable and bioabsorbable coatings have been reported. In non-bioabsorbable implantable medical devices, there have been attempts to reduce device drag using non-bioabsorbable low friction coatings or surface modification. However, device drag in bioabsorbable implantable medical devices, particularly occurring during implantation, or when there is articulation of surfaces, has been given little attention.

Accordingly, there is a need in this art for methods of reducing device drag in bioabsorbable implantable medical devices while maintaining the bioabsorbable nature of the devices.

SUMMARY OF THE INVENTION

Therefore, it is an object of this invention to provide methods of reducing device drag in bioabsorbable implantable medical devices while retaining the bioabsorbable characteristics of the device.

It is yet another object of the present invention to provide a coated substrate, wherein the substrate is a bioabsorbable material and the coating is a bioabsorbable lubricating material.

Accordingly, a coated bioabsorbable medical device is disclosed. The device has a first bioabsorbable contact surface. It also has a second a second bioabsorbable contact surface for engagement with the first contact surface. A bioabsorbable coating is disposed on at least a section of the second contact surface for reducing device drag.

Another aspect of the present invention is a coated bioabsorbable medical device. The device has a first bioabsorbable contact surface and a second bioabsorbable contact surface for engagement with the first contact surface. A bioabsorbable coating disposed on at least a section of both the first and second contact surfaces.

Yet another aspect of the present invention is a coated bioabsorbable medical device. The device has a first member having a first contact surface and a second member having a second contact surface. The second member engages the first member such that the first and second contact surfaces are approximated. A bioabsorbable coating is disposed on at least a portion of the second contact surface such that said coating engages the first contact surface. Optionally, the first contact surface also has a bioabsorbable coating disposed on at least a portion thereof.

Still yet another aspect of the present invention is a method of using the above-described medical devices.

These and other objects and advantages of the present invention will be apparent from the following description invention as illustrated in the drawings.

DETAILED DESCRIPTION OF THE INVENTION

The present invention relates to bioabsorbable coatings for bioabsorbable implantable medical devices to counteract device drag on the device surfaces during implantation or operation of the devices. The coatings reduce device drag in the devices while maintaining the bioabsorbable nature of the devices.

Figure 1:
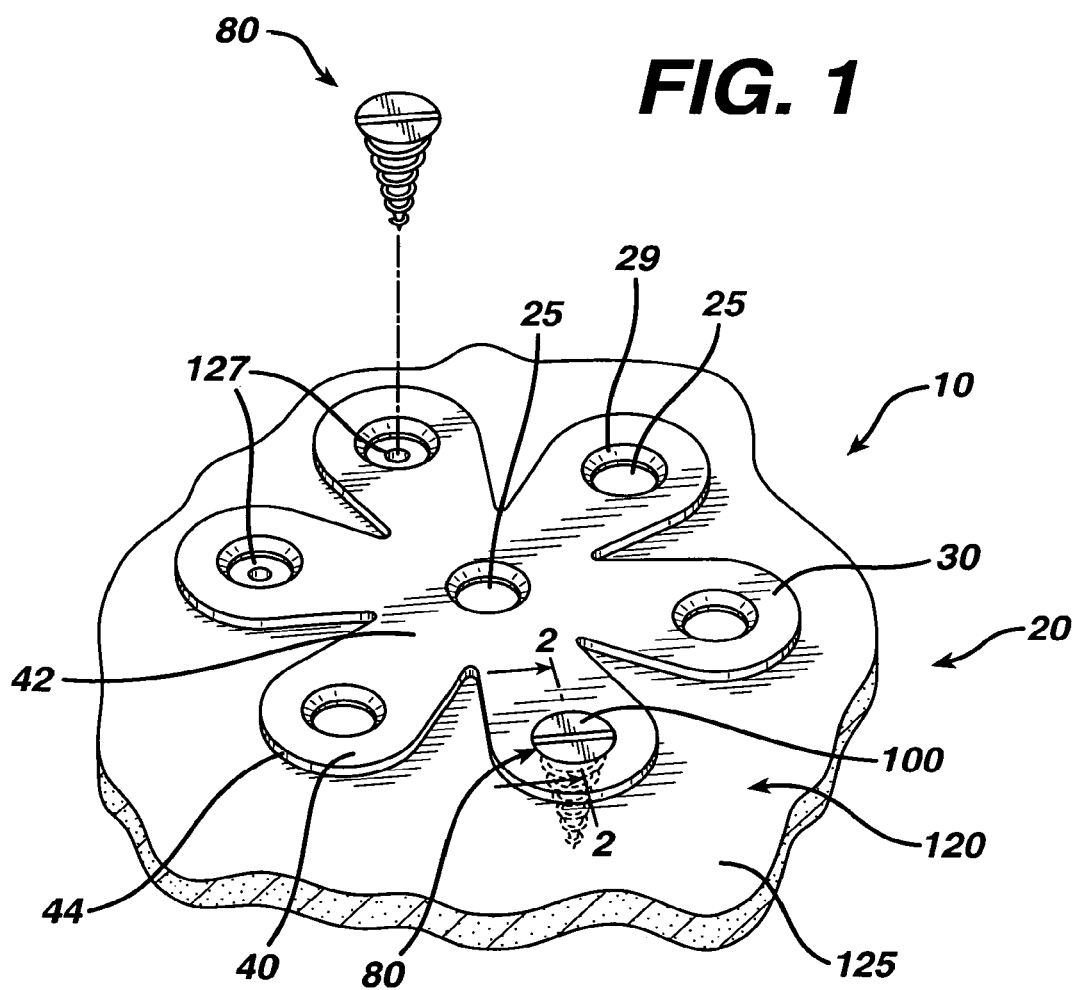
FIG. 1 is a perspective view of a bioabsorbable implantable bone plate system of the present invention having a bioabsorbable lubricating coating on its dragging surfaces in accordance with a first exemplary embodiment of the invention.

Referring to FIG. 1, a coated bioabsorbable implantable bone plate system of the present invention is illustrated. A similar bioabsorbable bone plate system without the lubricating bioabsorbable coating is described in U.S. Pat. No. 6,093,201, entitled "Biocompatible Absorbable Polymer Plating System for Tissue Fixation", which is incorporated by reference.

The bioabsorbable plate system 10 is seen to have a plate member 20 having top surface 30 and bottom surface 35. Member 20 is seen to have a plurality of radial projections 40 having proximal ends 42 and distal curved ends 44.

The radial projections 40 are seen to have fastener-receiving openings 42 extending therethrough. Plate member 20 is also seen to have a central fastener receiving opening 25 extending therethrough. Preferably the openings 25 are round but can have other geometric configurations. The openings 42 are seen to have sidewalls 27. The sidewalls 27 have beveled, angulated sidewall sections 29.

Figure 2:
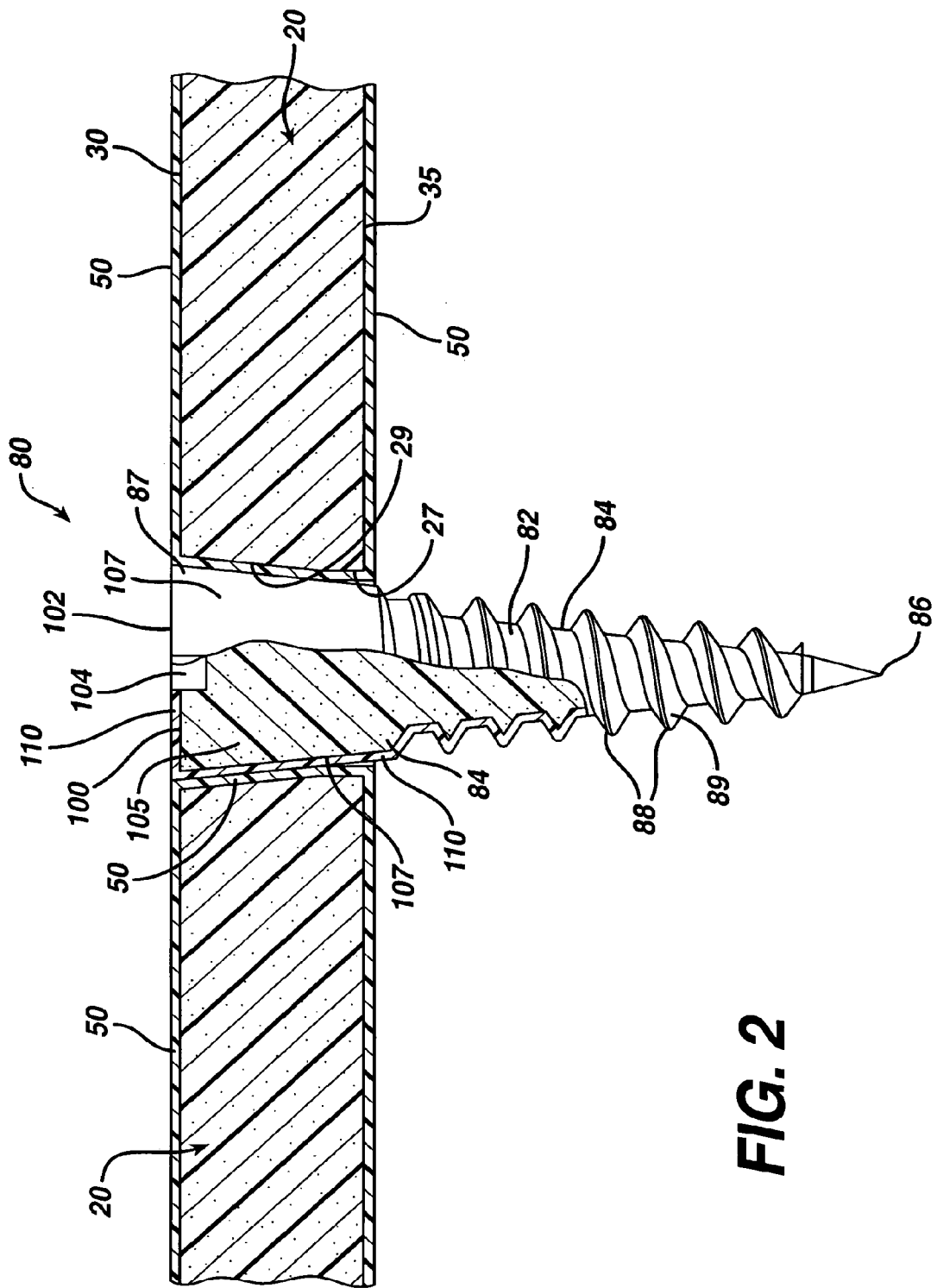
FIG. 2 is a cross-sectional view of the device system of FIG. 1 taken along View Line 2-2 showing the bone screws implanted in bone.

A cross-sectional view of plate member 20 is illustrated in FIG. 2. As seen in FIG. 2, the plate member 20 is seen to have coating 50 on top surface 30 and bottom surface 35. Coating 50 is also seen to be covering sidewalls 27 and angulated sections 29.

Referring to FIGS. 1 and 2, the plate system 10 is also seen to have a plurality of fasteners 80. The fasteners 80 are seen to be bioabsorbable bone screws having a root section 82 and a driving head 100. Root section 82 is seen to have exterior surface 84, pointed distal end 86, proximal end 87, and a plurality of thread flights 88 extending from exterior surface 84. The thread flights are seen to have exterior surface 89. The driving head 100 is seen to extend from proximal end 87 of root section 82. The driving head member 100 is seen to have a flat proximal surface 102 containing engagement cavity 104. Preferably the engagement cavity is a slot, but can have other configurations such as a cavity to accept conventional drivers such as Phillips head screw drivers, Torx screw drivers, Allen wrenches and the like and equivalents thereof. Head 100 is seen to have distal taping section 105 having outer surface 107. As seen in FIG. 2, the fastener 80 is seen to have coating 110 covering the outer surfaces.

When used in a surgical procedure, the surgeon prepares the patent in a conventional manner and then exposes the surface 125 of a bone 120 in the patient's body to which the bone plate is to be mounted using conventional surgical techniques. The surgeon then affixes the plate 20 to the bone surface 125 by drilling pilot holes 127 through openings 25 in a conventional manner by using conventional surgical drilling apparatus and techniques. The fasteners 80 are then inserted through openings 25 into pilot holes 127, and the surgeon screws the fasteners 80 into the bone 120 using conventional devices such as a screw driver, wrench, etc. As the fasteners 80 are being employed, the coating 110 on outer surfaces 84 and 89 and surface 107 of fastener 80 engage the coating 50 on the sidewalls 44 and 46 in openings 40. The presence of coatings 50 and 110 reduces device drag. Coating 110 may also reduce tissue drag as well in bone 120. If desired, in the practice of the present invention the surface of only one of the devices may be coated, and the surface of the other left uncoated.

Figure 3:
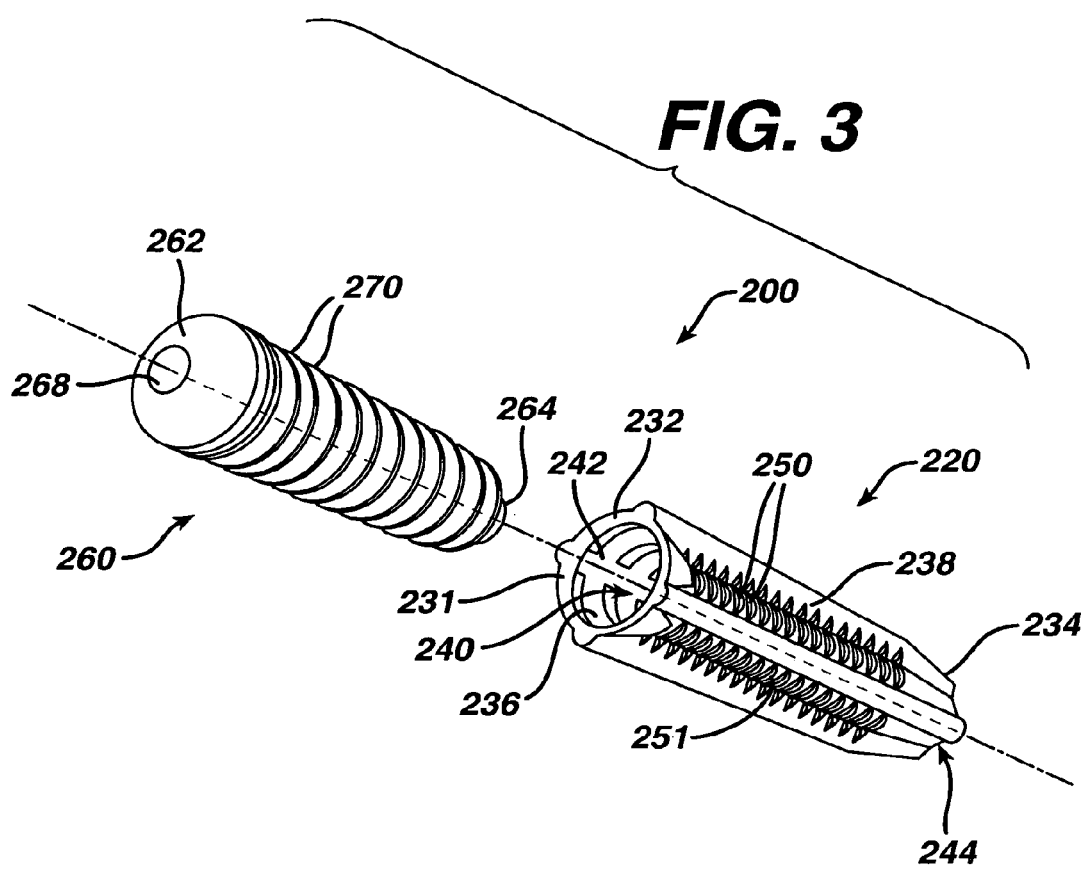
FIG. 3 is a perspective view of a bioabsorbable implantable ligament repair device of the present invention having bioabsorbable lubricating coatings on its dragging surfaces in accordance with a second exemplary embodiment of the invention.
Figure 4:
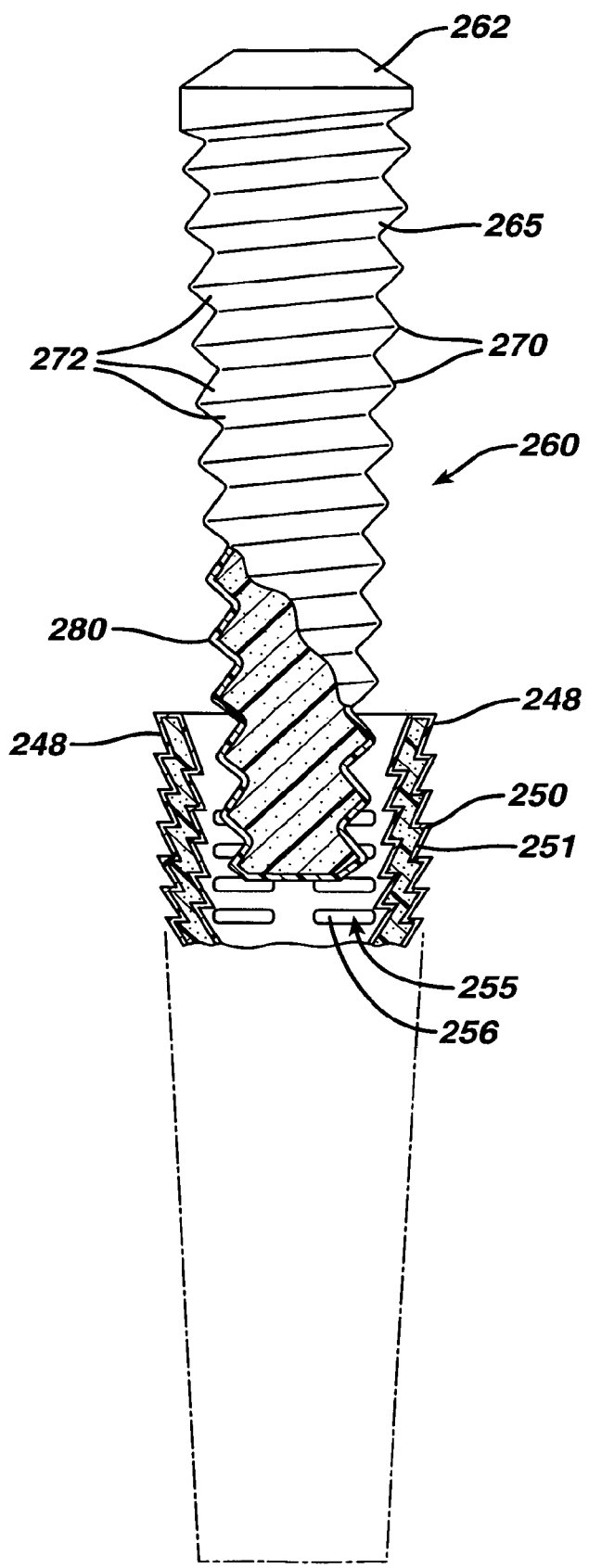
FIG. 4 is a partial cross-sectional view of the device of FIG. 3 taken along View Line 4-4; the distal end of the sheath member is shown in phantom lines.

FIGS. 3 and 4 illustrates a second embodiment of a bioabsorbable implantable medical device of the present invention, wherein the components have coated surfaces to reduce device drag. Referring to FIG. 3, a coated bioabsorbable graft ligament anchor system 200 is illustrated. A similar, but uncoated, bioabsorbable graft ligament anchor system is described in commonly assigned, copending U.S. patent application Ser. No. 09/966,766, entitled "Graft Ligament Anchor and Method for Attaching a Graft Ligament to a Bone", filed on Sep. 28, 2001, the disclosure of which is incorporated by reference.

Referring first to FIG. 3, the graft ligament anchor system 200 is seen to have a selectively radially expandable sheath member 220 and a sheath expanding member 260. Radially expandable sheath member 220 is seen to have wall 231, proximal end 232 and distal end 234, inner surface 236, outer surface 238 and central lumen 240. The sheath member 220 has proximal opening 242 and distal opening 244, both of which are in communication with lumen 240. Sheath member central lumen 240 is sufficiently sized to effectively receive and engage sheath-expanding member 260. Extending up from the outer surface of wall 231 are the ridged members 250 having outer surfaces 251 and inner pockets 255 having inner surfaces 256, said pockets 255 being in communication with lumen 240. The sheath member 220 is seen to have coating 248 upon the inner surface 236 and the outer surface 238, as well as on surfaces 256 and 251. Sheath expanding member 260 is seen to have proximal and distal ends 262 and 264, respectively.

The sheath expanding member 260 has outer surface 265 and a central longitudinal cannulation 268 extending therethrough. Extending outwardly from the outer surface 265 are a plurality of thread flights 270 having outer surfaces 272. The sheath expanding member 260 is also seen to have coating 280 upon outer surface 265 and outer surfaces 272.

During deployment of graft ligament anchor system 200, sheath expanding member 260 is inserted into sheath member central lumen 240 of expandable sheath member 220 and engages member 210 such that it expands radially. An insertion tool (not shown) is disposed into the central cannulation 268 of sheath expanding member 220 to drive expanding member 260 into sheath central lumen 240 by rotating the member 260. Rotation of member 260 causes threads 270 to engage pockets 255.

During insertion, outer surface 265 of sheath expanding member 260 and thread surfaces 272 drag along inner surface 236 of radially expandable sheath member 220 and inner surfaces 256 of pockets 255. This drag may result in friction, which could cause damage to some or all of these surfaces. The bioabsorbable coatings 248 and 280 of the present invention reduce the device drag and limit damage to these surfaces. Reduced device drag also reduces the insertion energy, and may be measured for example in insertion torque, of an insertion tool (not shown) as it drives expanding element 260 into sheath central lumen 240.

The bioabsorbable devices that have contact surfaces that may be coated according to the present invention are not limited to the bone screws, bone plates and ligament attachment systems described herein. Any bioabsorbable medical device having contact surfaces that engage each other, whether during insertion, after insertion, or both during and after insertion may be coated to decrease device drag. The devices include but are not limited to various types of conventional bioabsorbable medical devices such as orthopedic screws, bone plates, prostheses, anastomosis devices, grafts, suture anchors, orthopedic implants, spinal implants, joint replacements, vascular prosthetic devices, sort tissue implants, tissue fixation devices and the like.

The bioabsorbable medical devices of the present invention having contact surfaces will be made from conventional biocompatible, bioabsorbable polymers. They may be organic or inorganic, synthetic or natural. Examples of suitable biocompatible bioabsorbable polymers include biopolymers such as aliphatic polyesters, poly(amino acids), copoly (ether-esters), polyalkylenes oxalates, polyamides, poly (ethylene glycol), poly(iminocarbonates), polyorthoesters, polyoxaesters, polyamidoesters, polyoxaesters containing amine groups, poly(anhydrides), polyphosphazenes, biomolecules, and copolymers and blends thereof. For the purpose of this invention, aliphatic polyesters include but are not limited to homopolymers and copolymers of lactide (which includes lactic acid, D-, L- and meso lactide), glycolide (including glycolic acid), ε-caprolactone, paradioxanone (1,4-dioxan-2-one), trimethylene carbonate (1,3-dioxan-2-one), alkyl derivatives of trimethylene carbonate, monoglyceride polyesters, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. The biocompatible, bioabsorbable inorganics include ceramics composed of mono-, di-, tri-, alpha-tri, beta-tri, and tetra-calcium phosphate, hydroxyapatite, fluoroapatites, calcium sulfates, calcium fluorides, calcium oxides, calcium carbonates, magnesium calcium phosphates, bioglasses, and mixtures thereof. The devices of the present invention may also be made of composites of conventional bioabsorbable polymers and bioabsorbable inorganics. The devices of the present invention may additionally be made from natural biopolymers including collagen, elastin, alginate, chitin, hyaluronic acid, mono-, di- and polysaccharides, and gelatin.

Although it is desirable to coat the contact surfaces of both elements that are in contact or engagement, it is also within the purview of the present invention to coat only one engagement surface, or portions of one or both engagement surfaces to provide for increased lubricity and reduced device drag.

The coatings which are applied to the surfaces of the coated devices of the present invention will be sufficiently thick to provide effective lubricity and reduction of device drag. Of course the thickness will also depend upon the type of device and its application within the body, as well as the type of coating. However, for the devices described above, the thickness of the coatings will typically vary from about 1.0 to about 10.0 microns, more typically about 1.0 to about 5.0 microns, and preferably about 2 to about 5 microns.

When applying coatings to two contact surfaces, the same coating composition may used, or a different coating compositions may be used on each contact surface. If desired, multiple coats of the coatings may be applied. In addition, a base coat of a first coating composition may be applied over a contact surface, and a top coat of a second coating composition may be applied over the base coat.

The coatings useful in the practice of the present invention are low coefficient of friction biocompatible, bioabsorbable materials. They may be inorganic or organic compounds or blends of both. They may be low molecular weight compounds or biopolymers. They may be in either solid or liquid form, or a mixture of both, such as in a microdispersion, and may be either a naturally occurring or synthetic, or blends of both. Natural biopolymers include collagen, elastin, alginate, chitin, hyaluronic acid, mono-, di- and polysaccharides, and gelatin.

Examples of suitable biocompatible, bioabsorbable biopolymers that could be used include biopolymers such as aliphatic polyesters, poly(amino acids), copoly(ether-esters), polyalkylenes oxalates, polyamides, poly(ethylene glycol), poly(iminocarbonates), polyorthoesters, polyoxaesters, polyamidoesters, polyoxaesters containing amine groups, poly(anhydrides), polyphosphazenes, biomolecules, and copolymers and blends thereof.

For the purpose of this invention aliphatic polyesters include but are not limited to homopolymers and copolymers of lactide (which includes lactic acid, D-, L- and meso lactide), glycolide (including glycolic acid), ε-caprolactone, paradioxanone (1,4-dioxan-2-one), trimethylene carbonate (1,3-dioxan-2-one), alkyl derivatives of trimethylene carbonate, monoglyceride polyesters, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof.

The biocompatible, bioabsorbable inorganics include fine powders of ceramics composed of mono-, di-, tri-, alpha-tri, beta-tri, and tetra-calcium phosphate, hydroxyapatite, fluoroapatites, calcium sulfates, calcium fluorides, calcium oxides, calcium carbonates, magnesium calcium phosphates, bioglasses, and mixtures thereof.

Particularly preferred coating materials are bioabsorbable aliphatic polyester waxes made by the polycondensation of monoalkanoyl glycerides and common dicarboxylic acids (MGPEs=monoglyceride polyesters). These MGPE's have an aliphatic polyester backbone with pendant fatty acid ester groups and exhibit relatively low melting points ($T_m < 100°$ C.).

A second preferred coating material is a copolymer of epsilon-caprolactone and glycolide and glycolic acid. This composition is more fully discussed in U.S. Pat. No. 4,994,074, issued Feb. 19, 1991, the disclosure of which is hereby incorporated herein by reference. It is biocompatible and bioabsorbable, and approved by the FDA as a suture coating. Another preferred copolymer from this family of copolymers is a copolymer of 90% epsilon-caprolactone and 10% glycolic acid.

The inorganic fine powders mentioned above can also be added to the coating polymer or attached to the top surface of the coating polymer to reduce the friction further by reducing the contact surface area and/or through ball bearing mechanism. There are other side benefits for adding ceramic particles as they promote/induce bone growth and reduce tissue response by neutralizing the local acidic environment resulted by degradation of the absorbable polymer.

Various bioactive agents such as proteins (including short chain peptides), growth agents, chemotatic agents and therapeutic agents can be added to the coating prior to applying the coating to the implantable medical device. The variety of different therapeutic agents that can be used in conjunction with the present invention is vast. In general, therapeutic agents which may be administered include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMPs 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β I-III), vascular endothelial growth factor (VEGF)); and other naturally derived or genetically engineered proteins, polysaccharides, glycoproteins, or lipoproteins.

Coatings containing bioactive materials may be formulated by mixing one or more therapeutic agents with the coating. The therapeutic agents may be liquid, finely divided solid, or any other appropriate physical form. Optionally, the coating may include one or more additives, such as diluents, carriers, excipients, stabilizers or the like. The type of coating and bioactive concentration can be varied to control the release profile and the amount of bioactive dispensed. Upon contact with body fluids, the bioactive will be released. If the bioactive is incorporated into the coating, then the bioactive is released as the coating undergoes gradual degradation. This can result in prolonged delivery (for example, typically over 1 to 5,000 hours, preferably 2 to 800 hours) of sufficiently effective amounts of the bioactive.

Conventional coating techniques such as solution coating, powder coating and melt coating can be applied to coat the devices. An example for the copolymer of epsilon-caprolactone and glycolide and glycolic acid is solution coating. The coating polymer can be dissolved in an organic solvent such as ethyl acetate. Solution coating techniques such as dip coating, spraying, can then be used to coat the implantable medical devices.

For example, coating of the sheath expanding member 260 discussed above could be performed using a spray apparatus as described below. The apparatus includes: a mounting fixture attached to a motor to grip member 260 so that member 260 can be rotated around its longitudinal axis during the coating process. A conventional coating spray gun is mounted on a conventional motorized x-table that can be translated along the length of member 260. A liquid coating is placed in the spray gun, and the settings of the spray gun, the distance from the spray gun to the sheath expanding member 260, and the speeds of the rotating and translating motors can be adjusted so that the spraying is controllable and consistent to provide a uniform coating having a desired thickness.

The solvent used in dissolving the coating material often dissolves the bioabsorbable biopolymer used to make the device. In another embodiment, a substrate or base coat can be first coated on the surface of device to protect the direct contact of the solvent. The base coat should also be bioabsorbable and may be applied in the form of an aqueous solution. The aqueous base coat layer can be polyethylene glycol, modified starch, sucrose, dextrin, gelatin, acacia gum, poly (vinyl alcohol), hydroxypropyl methylcellulose, hydroxypropyl cellulose and carboxymethyl cellulose.

The following examples are illustrative of the principles and practice of the present invention, although not limited thereto. Numerous additional embodiments within the scope and spirit of the present invention will be apparent to those skilled in the art.

EXAMPLE 1

This example describes the process for making an exemplary bioabsorbable implantable medical device which may be used in accordance with an exemplary embodiment of the present invention.

Bioabsorbable graft ligament anchor systems 200 of the present invention, including a sheath member 220 and sheath expansion member 260 were manufactured using a conventional injection molding process. The polymer used to manufacture the radially expandable sheath members 220 was poly (lactic acid), or PLA, produced by Purac (Gorinchem, The Netherlands), with an I.V. of 1.87 dL/g as measured in chloroform. The expandable sheath members 220 were injection molded on a Niigata NN35MI injection molder with a barrel diameter of 18 mm. The polymer used to manufacture the sheath expanding elements was poly(lactic acid), or PLA, produced by Purac (Gorinchem, The Netherlands), with an I.V. of 3.2-4.0 dL/g as measured in chloroform. The sheath expanding members 220 were injection molded on a commercially available Engel injection molder with a 0.8 ounce barrel manufactured by Engel North America, Chicago, Ill.

A coating for the sheath expanding members 260 of the graft ligament anchor system 200 was then prepared. The coating was a copolymer of 90% epsilon-caprolactone and 10% glycolic acid (Ethicon Incorporated, Somerville, N.J.) with an I.V. of 0.45 dL/g as measured in hexafluoroisopropanol (HFIP) at 25° C. dissolved in ethyl acetate to a solution concentration of 7.5%. The coating was applied using a spray apparatus as described above. The x-table moving speed was set at 0.45 mm/sec. The rotating speed was set at 46 RPM. The distance of the spray nozzle was 1 inch from the outer threads of the expansion member 260. The spray gun (Model 150, Badger Air-Brush Co., Franklin Park, Ill.) opening setting was two rotations away from the minimum opening. A first sheath expanding member 260 was sprayed from the distal end to the proximal end and back, resulting in two passes of the sheath expanding member 260 through the spray nozzle. A second sheath expanding member 260 was sprayed as above, except the two-pass method was repeated three more times, resulting in eight passes of the member 260 through the spray nozzle. The coated devices were then put under vacuum at room temperature for one hour to remove the solvent. The amounts of coating were calculated by measuring the weights of the respective members 260 prior to and after the coating/drying steps. The sheath expanding member 260 which passed through the spray nozzle two times was coated with 1.0 milligram of coating, while the member 260 which passed through the spray nozzle eight times was coated with 4.5 milligrams of coating. These weights of coating represented between 0.065 and 0.290 weight percent of the coating/sheath expanding member 260 combination, respectively, for the two coated members 260 elements.

The torque of inserting the coated and uncoated sheath expanding members 260 into radially expandable sheaths 220 was then measured. Pilot holes, 11.5 mm in diameter, were drilled in a model bone material (15 PCDF Sawbone®, Pacific Research Laboratories, Inc., Vashon Island, Wash.). Four segments of Gore-Tex® Joint Sealant (W.L. Gore & Associates, Inc., Elkton, Md.) were placed in each quadrant of the pilot hole to simulate the hamstring tendons. A radially expandable sheath member 220 was inserted inside the pilot hole so that the joint sealant segments were between the sheath member 220 and the walls of the pilot hole. The distal end of a sheath expanding member 260 was inserted into the central lumen 240 of the expandable sheath member 220. A digital torque gauge (Digital Torque Gauge Model TMG, IMADA Incorporated, Northbrook, Ill.) was used to measure the insertion torque. The IMADA digital torque gauge comprised of a driver and a torque meter. The driver was connected to the torque meter so that the torque was measured and recorded in the torque meter. The driver was disposed into the central cannulation of the sheath expanding member 260. The insertion torque was measured using the torque meter. The peak insertion torque values required to drive the expanding member into the sheath central lumen 240 for an uncoated, and a two- and eight-pass coated expanding member 260 were 20, 6.9, and 7.9 in-lb, respectively. The test results showed improved lubricity, and reduced tissue drag for coated devices.

Although this invention has been shown and described with respect to detailed embodiments thereof, it will be understood by those skilled in the art that various changes inform and detail thereof may be made without departing from the spirit and scope of the claimed invention.

What is claimed is:

1. An implantable medical device, comprising:
   a first bioabsorbable implantable article having at least one fastener receiving opening, the fastener receiving opening having a contact surface with a first bioabsorbable lubricating coating disposed thereon; and
   a bioabsorbable fastener configured to be disposed within the at least one fastener receiving opening of the implantable article in mating engagement therewith, the bioabsorbable fastener having formed on an outer surface thereof a second bioabsorbable lubricating coating that is configured to contact and move relative to the first bioabsorbable lubricating coating on the contact surface of the first bioabsorbable implantable article.

2. The implantable medical device of claim 1, wherein the contact surface includes a sidewall of the at least one fastener receiving opening.

3. The implantable medical device of claim 1, wherein the first bioabsorbable implantable article includes a plate member, the plate member including a top surface and a bottom surface, wherein the at least one fastener receiving opening extends between the top surface and the bottom surface.

4. The implantable medical device of claim 1, wherein the first bioabsorbable implantable article is configured to maintain hard tissue in a desired position.

5. The implantable medical device of claim 4, wherein the hard tissue comprises bone.

6. The implantable medical device of claim 1, wherein the first bioabsorbable implantable article includes an expandable sheath member, the expandable sheath member including a proximal end, a distal end, an outer surface, and a central lumen defined by a wall extending between the proximal and distal ends.

7. The implantable medical device of claim 6, wherein the expandable sheath member includes a proximal opening at the proximal end that is in communication with the central lumen.

8. The implantable medical device of claim 6, wherein the contact surface includes an inner wall that defines the central lumen.

9. The implantable medical device of claim 1, wherein the bioabsorbable fastener is configured to expand the sheath member.

10. The implantable medical device of claim 1, wherein the first bioabsorbable implantable article is configured to maintain soft tissue in a desired position.

11. The implantable medical device of claim 10, wherein the soft tissue comprises tissue selected from the group consisting of tendon and ligament tissue.

12. The implantable medical device of claim 1, wherein the first coating is different than the second coating.

13. The implantable medical device of claim 1, wherein the first bioabsorbable lubricating coating is a continuous coating.

14. The implantable medical device of claim 1, wherein at least one of the first bioabsorbable implantable article and the bioabsorbable fastener are formed from a polymer selected from the group consisting of polylactic acid, polyglycolic acid, polycaprolactone, polydioxanone, trimethylene carbonate, and copolymers and blends thereof.

15. The implantable medical device of claim 1, wherein the bioabsorbable lubricating coating comprises a polymer selected from the group consisting of polylactic acid, polyglycolic acid, polycaprolactone, monoglyderide polyesters, and copolymers and blends thereof.

16. The implantable medical device of claim 1, wherein the bioabsorbable lubricating coating comprises 90/10 polycaprolactone/polyglycolide copolymer.

17. The implantable medical device of claim 1, wherein the bioabsorbable lubricating coating has a thickness in the range of about 1 microns to about 10 microns.

18. The implantable medical device of claim 1, wherein the second bioabsorbable lubricating coating contacts and moves relative to the first bioabsorbable lubricating coating, thereby providing reduced device drag.

* * * * *